United States Patent [19]
Rabinoff

[11] Patent Number: 5,716,941
[45] Date of Patent: *Feb. 10, 1998

[54] USE OF METHYL DONOR COMPOUNDS TO TREAT NEUROLOGICAL DYSFUNCTION ASSOCIATED WITH IMMUNE DEFECTS

[75] Inventor: Michael Rabinoff, Biddeford, Me.

[73] Assignee: Biogenesys, Wilmington, Del.

[*] Notice: The term of this patent shall not extend beyond the expiration date of Pat. No. 5,508,271.

[21] Appl. No.: 623,888

[22] Filed: Mar. 29, 1996

Related U.S. Application Data

[63] Continuation-in-part of Ser. No. 88,459, Jul. 7, 1993, Pat. No. 5,508,271.
[51] Int. Cl.$^6$ .......................... A61K 31/68; A61K 31/70; A61K 19/052
[52] U.S. Cl. .............................. 514/52; 514/903
[58] Field of Search .................... 514/52, 561, 903

[56] References Cited

U.S. PATENT DOCUMENTS 5,508,271  4/1996  Rabinoff ................................ 514/52

OTHER PUBLICATIONS

Kieburtz et al., "Abnormal Vitamin $B_{12}$ Metabolism in Human Immunodeficiency Virus Infection," Arch. Neurol. (1991), 48:312–314.
Pfohl et al., "Effect of Cobalamin Derivatives on In Vitro Enzymatic DNA Methylation: Methycobalamin Can Act as a Methyl Donor," Biochemistry (1991), 30:8045–8051.
Sakane et al., "Effects of Methyl-$B_{12}$ on the In Vitro Immune Functions of Human T Lymphocytes," J. of Clin. Immunology (1982), 2:101–109.
Scott and weir, "Hypothesis: The Methyl Folate Trap," The Lancent (1981), 337–340.
Surtees et al., "Association of Demyelination with Deficiency of Cerebrospinal-fluid S–adenosylmethionine in Inborn Erros of Methly–transfer Pathway," The Lancet (1991), 338:1550–1554.
Surtees et al., "Central–nervous–system Methyl–group Metabolism in Children with Neurological Complications of HIV Infection," The Lancet (1990), 335:619–621.
Yaqub et al., "Effects of methylcobalamin on Diabetic Neuropathy," Clinical Neurology and Neurosurgery (1992), 94:105–111.
Whitaker and Mitchell, "A Possible Role for Altered Myelin Basic Protein in Multiple Sclerosis," Annals of Neurology (1996), 40:3–4.
Kira et al., "Vitamin $B_{12}$ Metabolism and Massive–Dose Methyl Vitamin $B_{12}$ Therapy in Japanese Patients with Multiple Sclerosis," Internal Medicine (1994), 33:82–86.
Glass et al., "Hydroxocobalamin. I. Blood Levels and Urinary Excretion of Vitamin $B_{12}$ in Main After a Single Parenteral Dose of Aqueous Hydroxocobalamin, Aqueous Cyanocabalamin and Cyanocobalamin Zinc–Tannate Complex," Blood (1961), 18:511–521.
Beck, "Cobalamin and The Nervous System," The New England J. of Medicine (1988), 318:1752–1754.
Simpson and Miller, "The Treatment of Multiple Sclerosis with Massive Doses of Hydroxocobalamin," Neurology, 15:599–603, 1992.

*Primary Examiner*—Gary L. Kunz
*Attorney, Agent, or Firm*—Pamela Sherwood; Bozicevic & Reed LLP

[57] ABSTRACT

A method for treating a mammal with a demyelinating disease associated with an immunological disorder comprising administering methylcobalamin or cyanocobalamin.

3 Claims, No Drawings

USE OF METHYL DONOR COMPOUNDS TO TREAT NEUROLOGICAL DYSFUNCTION ASSOCIATED WITH IMMUNE DEFECTS

This is a continuing-in-part application of U.S. Ser. No. 08/088,459, filed Jul. 7, 1993 now U.S. Pat. No. 5,508,271.

TECHNICAL FIELD

The field of this invention is the use of methyl donor compounds to treat neurological and immunological disorders that arise in a mammalian host as the result of imbalances in methyl group metabolism.

BACKGROUND

The mammalian immune system is very complex; and disorder in its regulation may affect other organs in a number of ways. Lymphocytes and macrophages can directly attack cells of the body. Various metabolic products of these cells may be deleterious to tissue. Antibodies against autoantigens can accumulate in the kidneys and joints.

Several neurological disorders are thought to have an autoimmune component. In animal models for multiple sclerosis, T lymphocytes reactive with myelin basic protein can trigger disease symptoms. HIV infection is well known to have various neuropathies associated with it, where the degeneration of neural cells and demyelination may be directly caused by the action of cells in the immune system.

HIV infected patients with neurological disorders have increased neopterin levels in cerebrospinal fluid, possibly as a result of $\gamma$-interferon leading to increased synthesis of neopterin in monocytes and macrophages. Excess production of dihydroneopterin may lead to folate deficiency causing demyelination in the brain. Indolamine-2,3-dioxygenase activity is also increased by exposure to $\gamma$-interferon, leading to increased conversion of tryptophan to various metabolites, including quinolonic acid, which is neurotoxic.

Neural cells are sensitive to deficiencies in methyl group metabolism. At the present time there is not a definitive answer as to why this happens, although a number of theories have been postulated. The major pathway for methylation in humans is through S-adenosyl-methionine (SAM). The immediate precursor to SAM is methionine, which is produced by a pathway where 5-methyltetrahydrofolate transfers a methyl group to cobalamin, forming methylcobalamin, which in turn methylates homocysteine to form methionine. The cycling of homocysteine to methionine is required to maintain methylation homeostasis. It is possible that myelin basic protein is particularly unstable when there is a methionine deficiency. SAM is also required for the biosynthesis of phospholipids, which are required for neural function.

In the treatment of neurological disorders with methyl-donor compounds to restore normal methyl-group metabolism, it is beneficial to the host to use compounds that can positively affect the underlying immune disorder.

Relevant Literature

A review of the metabolic pathways for methylation, particularly those that function through S-adenosyl-methionine, can be found in Pfohl-Leszkowicz et al. (1991) *Biochemistry* 30:8045–8051, Effect of cobalamin derivatives on in vitro enzymatic DNA methylation: methylcobalamin can act as a methyl donor. The effects of a deficiency in components of this pathway is discussed in J. Scott et al. (1981) *The Lancet* Aug. 15, pp. 337–340, The methyl folate trap.

Surtees et al. (1991) *The Lancet* 338:1550–1554, Association of demyelination with deficiency of cerebrospinal-fluid S-adenosylmethionine in inborn errors of metabolism, discusses the treatment of methylation deficiencies for genetic defects.

Deficiencies of Vitamin $B_{12}$ metabolism in HIV patients is discussed in Kieburtz et al. (1991) *Arch NeUr.* 48:312–314, Abnormal Vitamin $B_{12}$ metabolism in Human Immunodeficiency Virus Infection, association with neurological dysfunction. Surtees et al. (1990) *The Lancet* 335:619–621, Central-nervous-system methyl-group metabolism in children with neurological complications of HIV infection, discusses the effect of methylation deficiencies in HIV infected children.

Sakane et al. (1982) *J. Clin. Immunol.* 2:101–109, discusses the effect of methylcobalamin on T lymphocytes in vitro. Yaqub et al. (1992) *Clinical Neurology and Neurosurgery* 94:105–111 determines the effect of methylcobalamin on diabetic neuropathy.

SUMMARY OF THE INVENTION

The subject invention provides a method for treating a host with neurological dysfunction associated with an immunological disorder, by the administration of a methyl donor compound, particularly methylcobalamin. The methyl donor compounds are also used to restore normal metabolic biochemical functions after immune mediated disruption of biochemical pathways.

DESCRIPTION OF THE SPECIFIC EMBODIMENTS

Methods and compositions are provided for treating neurological dysfunction that occur in association with an immunological disorder. Methyl donor compounds, or precursors thereof are able to stabilize or reverse neurological symptoms that occur as a result of immune associated imbalances in methyl group and folate metabolism. The methyl donor compounds are also able to positively affect the regulation of cells in the immune system, as a means of stopping the disease causing process. The improvement in the immune function is a further advantage for the patient.

The methyl donor compounds used in the treatment are those components and metabolites of the pathway which leads to synthesis of S-adenosyl-methionine in the body. Such compounds include 5-methyl tetrahydrofolate, methionine, S-adenosylmethionine, adenosyl-cobalamin, methylcobalamin, methionine, betaine, etc. Of particular interest is methylcobalamin, which has a positive effect on cells of the T lineage.

The compounds are used to treat immunological disorders, such as autoimmune disease, immunodeficiencies which result from infection or immunosuppressive drug treatment, lack of immune response to tumor cells, and the like. The compounds act to potentiate an immune response, increasing proliferation of lymphocytes in response to mitogenic signals and increasing the level of response by the lymphocytes.

Patients for which the subject therapy is indicated include those who are infected with human immunodeficiency virus (HIV). Particularly, HIV infected patients which have developed acquired immune deficiency syndrome (AIDS) or AIDS related complex (ARC) often have neurological complications which can benefit from methyl donor treatment. In a number of patients an increase in the blood concentration of T lymphocytes, particularly T4 positive lymphocytes, is seen after the subject therapy.

Autoimmune disorders with neurological complications that may be treated with the subject compounds are multiple sclerosis and myasthenia gravis. A quantitative increase in myelin—autoreactive T cells with the capacity to secrete IFN—gamma is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Another autoimmune disease that benefits from the immune regulatory effects of the methyl donor compounds is systemic lupus erythematosus (SLE). SLE is an autoimmune disorder in which IgG antibodies such as anti-dsDNA-IgG, anti-cardiolipin IgG, and anti-SS-A/Ro IgG are produced. Patients with SLE manifest various abnormalities, which probably reflect the immunopathological processes occurring concurrently in this multi-system disease. One consistent finding is defective IL-2 production by peripheral blood T-lymphocytes, which is independent of age or overall disease activity. Lupus nephropathy accompanied by diminished serum complement ($CH^{50}$) and a rise in antibodies against dsDNA is a frequent clinical problem, particularly during pregnancy, and may cause fetal death or intrauterine fetal growth retardation. Cardiovascular involvement occurs frequently, although it is often mild. A subset of systemic lupus erythematosis patients have low serum cobalamin levels. In addition, a larger percentage of SLE patients have high levels of transcobalamins (cobalamin binding proteins) in their plasma. It is known that one source of the transcobalamins are macrophages.

Other autoimmune diseases that are treated with the subject compounds are rheumatoid arthritis, polyarteritis nodosa, polymyositis and dermatomyositis, progressive systemic sclerosis (diffuse scleroderma), glomerulonephritis, myasthenia gravis, Sjogren's syndrome, Hashimoto's disease, Graves' disease, adrenalitis, hypoparathyroidism, pernicious anemia, diabetes, uveitis, pemphigus, pemphigoid cirrhosis, ulcerative colitis, myocarditis, regional enteritis, and adult respiratory distress syndrome.

The growth of tumors in a host may be due to breakdown in immune regulation and methyl group metabolism, and such tumors as sarcomas, lymphomas, adenocarcinomas, SCLC (small cell lung carcinoma), neuromas, melanomas, leukemias, basal cell carcinomas, and the like may benefit from the subject therapy. Particularly, slow growing solid tumors will be treated with methyl donor compounds. Leukemias and lymphomas respond to antagonists of the methyl donor compounds, which block DNA synthesis.

Neurological dysfunction that may be treated with the subject compounds include vacuolar myelopathy, demyelination, spasticity, encephalopathy, immune mediated encephalitis, subacute encephalitis, calcification of basal ganglia, numbness of fingers, hands and forearms, breakdown of myelin and disruption of the axon, pain and tingling in feet, distal diminution of sensation, minor motor neuron signs confined to the feet and diminished ankle reflexes, difficulty walking, spasticity in legs, weakness and uncoordinated legs, distal symmetrical polyneuropathy, inflammatory demyelinating polyneuropathy, multiple neuropathy, progressive polyradiculopathy, autonomic neuropathy, and the like. Conditions of particular interest, which are frequently associated with HIV infection, include vacuolar myelopathy, distal symmetrical polyneuropathy and demyelination. Demyelination is also associated with multiple sclerosis and EAE.

The mammalian host may be a human clinical patient, pet or research animal, including murine and other rodents, lagomorphs, porcine, feline, bovine, canine, primate, etc.

The subject compounds are administered in an amount effective to stabilize or reverse the neurological dysfunction. To further benefit the patient, the dose is sufficient to cause an upregulation in the immune system. This may be manifested as an increase in the number of T4 and/or T8 positive lymphocytes in an HIV infected patient, as an increase in anti-tumor or other T cell mediated activity, an increase in suppressor cells which effect a reduction in autoimmune activity, and the like.

The compounds, 5-methyltetrahydrofolate, methionine, S-adenosyl methionine, adenosylcobalamin, methylcobalamin, methionine, betaine, etc., are administered to a host in a physiologically acceptable carrier.

The compounds may be administered in a variety of ways, orally, parenterally, or by inhalation. For oral administration, the pharmaceutical composition will generally contain from about 5–100% by weight of the active material, for other applications, the composition will generally have from about 0.05–50 wt. % of the active material. For injection, the methyl donor compounds may be injected subcutaneously, intramuscularly, intraperitoneally, intravascularly, etc. Depending upon the manner of introduction, the compounds may be formulated in a variety of ways. Carriers include excipients, sugars, alum, dimethyl sulfoxide, etc. Of particular interest are methods of administration that will target the drug to the nervous system, either by direct injection, site specific drug delivery, prodrugs or carriers that target neural tissue or increase penetration of the blood brain barrier, and the like.

The pharmaceutical compositions can be prepared in various forms, such as granules, tablets, pills, capsules, suspensions, and the like. Pharmaceutical grade organic or inorganic carriers and/or diluents suitable for oral use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The subject compositions will generally be administered from as often as daily for initial treatment, to as infrequently as monthly for maintenance level treatment. The amount may vary with the general health of the patient, the response of the patient to the drug, whether the methyl donor compound is used by itself or in combination with other drugs, and the like. Daily administrations may be one or more times, usually not more than about four times, particularly depending upon the level of drug which is administered.

Methylcobalamin treatment will usually be from 3 times daily to once weekly administration. The preferred method of administration in i.m. injection. Maintenance treatment may be administered monthly. The dose at each administration will usually be from about 0.1 micrograms to 10,000 milligrams, more usually from about 1 microgram to 2500 milligrams. Oral administration may be as much as 10,000 milligrams. Usually the dose for treating a demyelinating disease associated with immune dysfunction will be at least about 0.033 milligrams per gram body weight, and may be as much as 0.33 milligrams per gram body weight. L-methionine will usually be administered orally. The dosage may be from 1 g/day to as much as 25 g/day, and will usually be from 1 to 10 g/day, more usually from 3 to 9 g/day. Dosage for betaine will be from 25 mg/day to as much as 15 g/day, usually 1 to 5 g/day, more usually about 3 g/day. Dosage for 5 methyl-tetrahydrofolic acid will be from 100 μg/day to as much as 150 mg/day, and will usually be from 100 μg/day to 25 mg/day, more usually from 500 μg/day to 5 mg/day. Dosage from S-adenosyl-methionine will be from 1 to 1000 mg/day, usually from 10 to 100 rag/day, more usually from 200 to 400 mg/day.

EXPERIMENTAL

Example 1

Treatment of HIV Infection

Ten AIDS patients with associated neurological dysfunction were treated over a three month period with methylcobalamin. Methylcobalamin administration was intramuscular (IM) unless otherwise noted. Plan A gave 1000 micrograms of methylcobalamin every other day for two weeks, then 250 micrograms weekly for a month, then 1000 micrograms per month. Plan gave 1000 micrograms methylcobalamin weekly for three months. The methylcobalamin was stored at 4° C., and used within 24 hours of dilution. For intramuscular injection the methylcobalamin was dissolved in normal saline, for intravenous injection the methylcobalamin was dissolved in Ringer's or lactated Ringer's solution. Patients were treated with AZT or oral methionine as noted. The results are presented in Table 1.

TABLE 1

| Subject | pre-treatment T4+ cells/mm³ | pre-treatment T8+ cells/mm³ | post-treatment T4+ cells/mm³ | post-treatment T8+ cells/mm³ | Treatment with AZT | Methyl-cobalamin Treatment | Treatment with oral Methionine | Age of patient | Neurological Symptoms after treatment |
|---|---|---|---|---|---|---|---|---|---|
| 1 | 162 | 716 | 210 | 747 | yes | Plan A IM | — | 35 | reduction in depressed ankle reflexes, reduction in distal weakness |
| 2 | 197 | 674 | 242 | 698 | no | Plan A IM | — | 32 | reduction in loss of position and vibratory sense, reduction in distal weakness |
| 3 | 142 | 705 | 191 | 742 | yes | Plan A IM | 3–9 gm/day | 41 | marked reduction in spasticity, reduction in distal weakness, reduction in loss of position and vibratory sense |
| 4 | 184 | 646 | 235 | 673 | yes | Plan B IM or IV | — | 38 | elimination of pins and needles sensation and muscle weakness |
| 5 | 262 | 722 | 319 | 771 | no | Plan B IM | — | 37 | reduction in loss of position and vibratory sense, reduction in distal weakness |
| 6 | 310 | 947 | 335 | 981 | no | Plan B IM | — | 34 | elimination of pins and needles sensation and muscle weakness |
| 7 | 121 | 708 | 167 | 729 | yes | Plan A IM or IV | 3–9 gm/day | 41 | marked reduction in spasticity, reduction in distal weakness |
| 8 | 109 | 669 | 178 | 714 | yes | Plan A IM or IV | 3–9 gm/day | 38 | marked reduction in ataxia, reduction in distal weakness, reduction of loss of position and vibratory sense |
| 9 | 177 | 596 | 251 | 635 | yes | Plan A IM | — | 37 | elimination of pins and needles sensation and muscle weakness |
| 10 | 216 | 648 | 269 | 691 | yes | Plan A IM | — | 40 | reduction in depressed ankle reflexes, reduction in distal weakness |

|  | T4+ cells/mm³ | T8+ cells/mm³ | T4/T8 | Statistical Significance |
|---|---|---|---|---|
| Pre-treatment | 188 | 703.1 | 0.267 | Difference in pre- and post-T4+ population; paired, 2 tail T-test; $p < 0.001$ |
| Post-treatment | 239.7 | 738.1 | 0.325 | Difference in pre- and post-T8+ populations; paired, 2 tail T-test; $p < 0.001$ |

Plan A gave 1000 micrograms of methylcobalamin every other day for two weeks, then 250 micrograms weekly for a month, then 1000 micrograms per month. Plan B gave 1000 micrograms methylcobalamin weekly for three months. Blood was taken from patients, stained for T4 or T8 surface antigen and the number of lymphocytes counted (columns of T4+ and T8+ cells).

Other drugs may be used in accordance with conventional treatments. For HIV infection or other retroviral infection, these include AZT, ddI, ddC, oral methionine, steroids, vitamin $B_{12}$, etc. The additional drugs may be administered separately or in conjunction with the methyl donor compounds and may be formulated in the same formulation. Treatment of multiple sclerosis may include the additional drugs interferon-β, or other immunomodulatory therapies.

The following examples are offered by way of illustration and not by way of limitation.

It is evident from the above results, that treatment of patients with AIDS associated neurological dysfunction with methylcobalamin provides for substantial improvements in the patient neurological symptoms, as well as increasing the concentration of T lymphocytes in the blood.

Example 2

Treatment of EAE

Methods

Female SJL/J mice of 4–6 weeks of age were purchased from the Jackson Laboratories (Bar Harbor, ME) and housed in the animal quarters of the E. K. Shriver Center. They were maintained in accordance with U.S. Dept. HHS publication 85-23.

Proteolipid protein peptide p139–151 (HSLGKWLGHPDKF was prepared according to the published sequence, except that serine was substituted for cysteine at position 140. The peptide was synthesized with a C terminal amide and was >90% pure as determined by mass spectroscopy and high performance liquid chromatography.

Mice were injected subcutaneously in the flanks and in the nape of the neck with an emulsion consisting of equal parts of Complete Freund's Adjuvant (CFA) containing 400 μg of H37Ra (Difco laboratories, Detroit, MI) and antigen in PBS. Each mouse was also injected i.v. on day 0 and day 3 with $10^9$ heat killed *Bordetella pertussis* bacilli (Mass. Public Health Laboratories, Boston, Mass.). Experimental groups were injected subcutaneously on day 8 or days 8 and 12 with the following test compounds (all from Sigma Chemical Co., St. Louis, Mo.): cobalamine, methylcobalamine, betaine, methionine, S-methyl tetrahydrofolate, histidine, glycine. Test compounds were used at a standard dose of 0.33 mg/g body weight. Mice were observed daily for clinical signs of disease and scored as follows: grade 0, no signs; grade 1, decreased tail tone or slightly clumsy gait; grade 2, limp tail and hind limb weakness (waddling gait) and/or poor righting ability; grade 3, severe hind limb weakness; grade 4, limb paralysis; 5, moribund state.

Animals were sacrificed at day 6, 12 or 14 post-immunization. Following anesthetization with ether, mice were perfused intracardially with 0.9% saline and brains and spinal cords were removed. Central nervous system tissues were removed, fixed in 10% neutral buffered formalin and processed routinely for paraffin embedment. Sections stained with Luxol fast blue-hematoxylin and eosin stain were evaluated without the observer's knowledge of the treatment or clinical status of the animals. Stained inflammatory loci (≥20 inflammatory cells) were counted in leptomeninges and CNS parenchyma as described by Sobel et al. (1990) *J. Exp. Neur.* 49:468–479.

The treatments were as follows: methylcobalamin day 8; methylcobalamin day 8+12; cyanocobalamin day 8; cyanocobalamin day 8+12; 0.16 mg/g (50% dose) cyanocobalamin day 8; 0.033 mg/g (10% dose) cyanocobalamin day 8; 5 methyl $H_4$ folate day 8+12; histidine day 8+12; 0.033 mg/g (50% dose) cyanocobalamin day 8; 0.16 mg/g (10% dose) cyanocobalamin day 8; betaine day 8; methionine day 8; cyanocobalamin day 0 and PLP 139–151 day 7; cyanocobalamin day 0 and PLP 139–151 day 0; 5-methyl H4 folate day 8+12; histidine day 8+12; glycine day 8+12.

The results are shown in Table 2.

TABLE 2

| Treatment | clinical score avg | T-test | hist. score avg. | T-test | meninges avg. | T-test | parenchyma avg. | T-test |
|---|---|---|---|---|---|---|---|---|
| Methylcobalamin Day 8; n = 9 | 0.111 | 0.0018 | 0.55 | 0.0006 | 0.44 | 0.0009 | 0.111 | 0.0009 |
| Methylcobalamin Day 8 and 12; n = 9 | 0 | 0.0014 | 1.33 | 0.0006 | 0.66 | 0.001 | 0.67 | 0.0009 |
| Cyanocobalamin Day 8; n = 5 | 0 | 0.0005 | 0 | <0.0005 | 0 | 0.0008 | 0 | 0.0006 |
| Cyanocobalamin Day 8 + 12; n = 5 | 0 | 0.0005 | 0 | <0.0005 | 0 | 0.0008 | 0 | 0.0006 |
| 50% dose Cyanocobalamin; n = 4 | 0.5 | 0.001 | 170 | 0.18 | 59.3 | 0.38 | 108.25 | 0.04 |
| 10% dose Cyanocobalamin; n = 4 | 1.25 | 0.123 | 172.75 | 0.07 | 68.75 | 0.28 | 106.5 | 0.03 |
| 5 methyl tetrahydrofolate day 8 + 12; n = 5 | 3.6 | 0.02 | 182.8 | 0.11 | 83.2 | 0.14 | 99.6 | 0.26 |
| histidine day 8 + 12; n = 5 | 1.8 | 0.26 | 87.6 | 0.12 | 40 | 0.16 | 47.6 | 0.1 |

T-test analysis was performed with a control clinical average score of 2.375, n = 8; a control histological score of 130.625; n = 8; a control meninges score of 55.375, n = 7; and a parenchyma average of 75.25, n = 7.

| Treatment | clinical score avg | T-test | hist. score avg. | T-test | meninges avg. | T-test | parenchyma avg. | T-test |
|---|---|---|---|---|---|---|---|---|
| Betaine Day 8; n = 4 | 0.75 | 0.01 | 191.5 | 0.38 | 92.5 | 0.2 | 94 | >0.5 |
| Methionine Day 8; n = 4 | 0.75 | 0.01 | 194 | >0.5 | 89 | >0.5 | 111 | >0.5 |
| Cyanocobalamin Day 0, PLP day 7 | 0 | <0.005 | | | | | | |
| Cyanocobalamin Day 0, PLP day 0 | 1.4 | 0.03 | 181 | >0.5 | 73 | >0.5 | 108 | >0.5 |
| Glycine day 8 + 12 | 0.6 | 0.003 | 166 | >0.5 | 82 | >0.5 | 112 | >0.5 |

T-test analysis was performed with a control clinical average score of 3.67, n = 9; a control histological score of 185.2; n = 9; a control meninges score of 85.3; n = 9 and a control parenchyma score of 99.8; n = 9.

All control animals injected with proteolipid protein (amino acids 139–151, with serine substituted for cysteine at position 140) became paralyzed. However, those injected with methylcobalamin on day 8, or days 8 and 12 after innoculation with the PLP didn't develop paralysis, and on immunohistochemical analysis did not exhibit the demyelination that was present in the controls.

It can be seen from the data presented in Table 2 that methylcobalamin and cyanocobalamin provide significant protection compared to the controls. A surprising finding is that a 50% or 10% dose of cyanocobalamin is less protective than the high dose.

It is probable that methylcobalamin will retain its protective effect at lower doses. Where there is a defect in the production or transport of methylcobalamin, 5-methyl tetrahydrofolate can't be converted in the cell to tetrahydrofolate, and folates cannot get into the cell. This is known as the methyl folate trap. This is supported by the demonstrating an adverse effect with histidine, and the improvement that is seen with glycine, because glycine permits the regeneration of tetrahydrofolate.

Under physiological conditions, the vast majority of cobalamin is converted into methylcobalamin. After an injection of cyanocobalamin, blood levels of methyl cobalamin increase to a much greater extent than do cyanocobalamin levels. If there is a biochemical block that interferes with the involved pathways, then at lower doses methylcobalamin might have a greater effect than cyanocobalamin.

Example 3

Treatment of MRL-lpr/lpr Mice

Methyl donor deficiency may be involved in the development of a subset of systemic lupus erythematosus (SLE) cases. The purpose of this study is to determine whether folate, cobalamin and methyl donor supplementation prevent a genetically induced SLE-like disease process in an animal model. Disease progression was monitored by the characteristic increase in blood urea nitrogen in affected individuals. The presence of various surface antigens (CD4, CD8, thy 1.2, and B220) on lymphocytes was also analyzed by immunoflorescence staining.

Methods

Experiments were performed on MRL-lpr/lpr mice. MRL-lpr/lpr mice develop a generalized autoimmune disease that includes increased autoantibody production, glomerulonephritis, and development of lymphadenopathy. The mice were purchased at 5 weeks of age, and housed individually until 18 weeks of age. After this time, rapid deterioration normally occurs, and usually half are dead by about five months. 64 mice were used, divided into groups of 8 mice each.

One-half of each group received weekly injections of the indicated test chemical, and one-half received monthly injections. The controls were injected with saline alone. Dosage levels were as follows:

| | |
|---|---|
| folic acid | 33 mg/kg administered IP |
| 5-methyl tetrahydrofolic acid | 33 mg/kg administered IP |
| cyanocobalamin | 330 mg/kg administered IP |
| methyl cobalamin | 330 mg/kg administered IP |
| I-methionine | 180 mg/kg administered IP |
| S-adenosyl-L-methionine | 320 mg/kg administered IP |
| betaine | 25 mg/kg administered IP |

Results

The groups were as follows:

Mice no. 1–8 control. 3 mice died before the end of the experiment.

Mice no. 9–16 folic acid

Mice no. 17–24 5-methyl tetrahydrofolic acid

Mice no. 25–32 cyanocobalamin

Mice no. 33–40 betaine

Mice no. 41–48 methyl cobalamin

Mice no. 49–56 l-methionine

Mice no. 57–64 S-adenosyl-l-methionine

The data are shown in Table 3. The control animals had significantly higher BUN scores, as measured by Azostix, than the folic acid and betaine groups. The control group had a significantly higher percentage of CD4−CD8−cells than the folic acid and methyl cobalamin groups. The control group had a significantly higher percentage of B220+ cells than the 5-methyl tetrahydrofolic acid and the I-methionine groups. Also, the control group had a higher percentage of CD4−CD8−B220+ cells (as measured by product of percent gated CD4−CD8− and thy 1.2+B220-cells) than the folic acid and methionine groups, with methyl cobalamin $p<0.059$. In addition, 3 of the control group died during the experiment, equalling the total deaths from the other 7 groups.

The unusual TCR alpha/beta+ CD4−CD8−B220+ cells that accumulate in these mice are probably descendents of previous activated peripheral T cells that failed to undergo physiological death at the end of an immune response. These cells are correlated with the lymphoproliferative SLE like disease, with thymic defects of maturation, B cell defects, hypergammaglobulinemia and autoantibody production, and autoimmune disease involving the CNS, kidney, pneumonitis, synovitis and arthritis.

TABLE 3

| Treatment | BUN score avg | T-test | % B220$^+$ | T-test | % CD4$^-$CD8$^-$ | T-test | % of B220$^+$ that are Thy-1$^+$ CD4$^-$CD8$^-$ | T-test |
|---|---|---|---|---|---|---|---|---|
| Control | 41 | | 75 | | 28.4 | | 22 | |
| folic acid | 32 | 0.02 | 67 | 0.08 | 6.8 | 0.03 | 5 | 0.03 |
| 5-methyl tetrahydrofolic acid | 43.8 | 0.3 | 66 | 0.02 | 15.6 | 0.11 | 10 | 0.09 |
| cyanocobalamin | 46.4 | 0.14 | 63 | 0.05 | 18.13 | 0.21 | 9 | 0.08 |
| betaine | 35 | 0.03 | 72 | 0.29 | 14.12 | 0.09 | 9 | 0.08 |
| methyl cobalamin | 38.6 | 0.3 | 78 | 0.18 | 9.81 | 0.05 | 7.7 | 0.058 |
| I-methionine | 47.5 | 0.05 | 58 | 0.04 | 12.3 | 0.089 | 6 | 0.04 |
| S-adenosyl-I-methionine | 37.6 | 0.27 | 77 | 0.31 | 12.26 | 0.1 | 10 | 0.1 |

BUN scores were determined with azostix, according to the manufacturers instructions. The percent of cells expressing different surface markers was determined by antibody staining and FACS analysis on peripheral blood samples.

The subject treatment is shown to reduce the numbers of CD4$^-$CD8$^-$B220$^+$ cells that are associated with the lymphoproliferative condition. Folate in particular is effective in suppressing disease symptoms.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a mammalian host with a demyelinating disease associated with an immunological disorder, said method comprising:

administering to said host methylcobalamin or cyanocobalamin in an amount effective to stabilize or reverse said demyelinating disease.

2. A method according to claim 1, wherein said immunological disorder is multiple sclerosis or experimental autoimmune encephalitis.

3. A method according to claim 2, where said amount effective to stabilize or reverse said demyelinating disease is 1 microgram to 2500 milligrams.

* * * * *